United States Patent
Richter

(10) Patent No.: US 8,052,733 B2
(45) Date of Patent: **\*Nov. 8, 2011**

(54) SINGLE OPERATOR STENTING SYSTEM

(75) Inventor: Jacob Richter, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 165 days.

This patent is subject to a terminal disclaimer.

(21) Appl. No.: 11/615,634

(22) Filed: Dec. 22, 2006

(65) Prior Publication Data
US 2007/0150043 A1    Jun. 28, 2007

Related U.S. Application Data

(63) Continuation of application No. 10/228,052, filed on Aug. 27, 2002, now Pat. No. 7,172,619.

(60) Provisional application No. 60/314,671, filed on Aug. 27, 2001.

(51) Int. Cl.
*A61F 2/06* (2006.01)

(52) U.S. Cl. ...................................... 623/1.11

(58) Field of Classification Search .......... 623/1.11–2.1
See application file for complete search history.

(56) References Cited

U.S. PATENT DOCUMENTS

| | | | |
|---|---|---|---|
| 4,787,884 A | 11/1988 | Goldberg | |
| 4,877,031 A | 10/1989 | Conway et al. | |
| 4,927,413 A | 5/1990 | Hess | |
| 5,117,838 A * | 6/1992 | Palmer et al. | 600/585 |
| 5,383,853 A | 1/1995 | Jung et al. | |
| 5,409,470 A | 4/1995 | McIntyre | |
| 5,443,500 A | 8/1995 | Sigwart | |
| 5,456,667 A | 10/1995 | Ham et al. | |
| 6,013,085 A | 1/2000 | Howard | |
| 6,117,104 A * | 9/2000 | Fitz | 604/96.01 |
| 6,183,420 B1 * | 2/2001 | Douk et al. | 600/462 |
| 6,416,494 B1 * | 7/2002 | Wilkins | 604/96.01 |
| 6,514,191 B1 | 2/2003 | Popowski et al. | |
| 6,709,440 B2 * | 3/2004 | Callol et al. | 606/108 |
| 7,172,619 B2 | 2/2007 | Richter | |
| 7,384,411 B1 * | 6/2008 | Condado | 604/96.01 |

FOREIGN PATENT DOCUMENTS

| | | |
|---|---|---|
| EP | 382014 A1 | 8/1990 |
| EP | 0 965 311 A2 | 12/1999 |
| EP | 1 101 455 A2 | 5/2001 |
| EP | 1 101 455 A3 | 6/2003 |

(Continued)

OTHER PUBLICATIONS

Office Actions and Responses to Office Actions of related U.S. Appl. No. 10/228,052, now Patent No. 7,172,619.

(Continued)

*Primary Examiner* — Suzette J Gherbi
(74) *Attorney, Agent, or Firm* — Cadwalader Wickersham & Taft LLP

(57) ABSTRACT

Embodiments of a stent system include a catheter is made with only one lumen leading to a balloon. An arrangement is provided to easily lock a short wire in place at the distal end of the balloon. Multiple wires of different properties can be included in a package containing the stent and the delivery catheter, such that the physician will be able to choose the right wire tip according to the lesion and vessel treated and attach it at the distal tip of the balloon before beginning the stenting procedure.

15 Claims, 1 Drawing Sheet

FOREIGN PATENT DOCUMENTS

| | | |
|---|---|---|
| JP | H05-011996 | 1/1993 |
| JP | H06-009612 | 1/1994 |
| JP | H09-503678 | 4/1997 |

OTHER PUBLICATIONS

Notice of Allowance dated Sep. 27, 2006.
Amendment and Response to Non-Final Rejection with Extension of Time dated Aug. 18, 2006.
Non-Final Rejection dated Apr. 18, 2006.
Request for Continued Examination, dated Mar. 3, 2006.
Notice of Appeal with Extension of Time dated Jan. 10, 2006.
Advisory Action dated Dec. 28, 2005.
Amendment and Response to Non-Compliant Notice and dated Sep. 13, 2005.
Notice of Non-Compliant Amendment dated Aug. 30, 2005.
Amendment and Response to Final Rejection dated Aug. 11, 2005.
Final Rejection dated Jul. 11, 2005.
Advisory Action dated Apr. 28, 2005.
Appeal Brief and Extension of time dated Apr. 25, 2005.
Amendment and Response to Final Rejection dated Mar. 25, 2005.
Advisory Action dated Dec. 17, 2004.
Amendment and Response to Final Rejection dated Nov. 29, 2004.
Final Rejection dated Sep. 29, 2004.
Response & Amendment to Non-Final Rejection dated Jun. 8, 2004.
Non-Final Rejection dated Mar. 17, 2004.
Preliminary Amendment dated Mar. 19, 2003.

* cited by examiner

SINGLE OPERATOR STENTING SYSTEM

CROSS REFERENCE TO RELATED CASES

Applicant claims the benefit of U.S. Provisional Ser. No. 60/314,671 filed Aug. 27, 2001. This application is a continuation of U.S. application Ser. No. 10/228,052, filed on Aug. 27, 2002 and issued as U.S. Pat. No. 7,172,619 on Feb. 6, 2007.

FIELD OF THE INVENTION

The present invention relates generally to intravascular stents for implanting into a living body. In particular, the present invention relates to an improved balloon catheter for inserting intravascular stents into a vessel in the body.

BACKGROUND OF THE INVENTION

Intravascular stents having a constricted diameter for delivery through a blood vessel and an expanded diameter for applying a radially outwardly extending force for supporting the blood vessel are known in the art. Both self-expandable stents and balloon expandable stents are well known.

In conventional stent mounting and securing procedures, the stent is usually first slid over the distal end of a balloon catheter so that the expandable balloon is disposed within the longitudinal bore of the stent. The stent is then crimped to mount or secure the stent and maintain its position with respect to the expandable balloon as the balloon catheter is advanced to the target area.

Typical catheters for interventional angioplasty are based on a catheter that rides on a guide wire. The guide wire has some characteristics of flexibility and pushibility that may vary along its length. The catheter (balloon catheter) also has some characteristics of flexibility and stiffness that may vary along its length. The variations of flexibility and pushibility do not match each other as the catheter tracks along different sections of the wire. Also, the profile of the catheter has to permit the free ride of an internal lumen in the catheter over the wire, resulting in a bigger profile and less flexible catheter shaft. The tip of the balloon catheter may latch on plaque when pushed to the vessel wall by the guide wire and thus prevent insertion through constricted areas and through another stent.

An arrangement which does not use a guide wire that slides through the balloon of the balloon angioplasty catheter is disclosed in European Patent Application EP 1 101 455 A2. In that arrangement, a stent delivery system is provided for percutaneous insertion into a vessel of the human body in order to place a balloon expandable stent at the site of an obstruction in the vessel. The stent delivery system includes a balloon angioplasty catheter having a distal section with an inflatable balloon located at the distal section of the balloon angioplasty catheter. A balloon expandable stent is co-axially mounted on the inflatable balloon. A flexible guide wire is fixedly attached to and extends distally from the distal section of the balloon angioplasty catheter.

In today's arena where direct stenting has become very popular and no other catheter is threaded on the guide wire before, or after the stent delivery system, such a stent delivery system that is combined with a wire tip at its forward end becomes quite reasonable. It can solve the problems of optimal flexibility transition, optimal profile and elimination of "steps" between the catheter tip and the wire. Furthermore, it can make for a faster and less traumatic procedure with one insertion instead of two (wire and then catheter). Thus, a catheter with a wire tip at the length of a single operator catheter does not require a second hand for holding the wire during the insertion of the catheter, and thus forms a single operator stent system.

However, one of the disadvantages of an arrangement such as that shown in EP 1 101 455 A2 is that today there are at least three different classes of guide wires used. These differ in their overall flexibility and the arrangement of different sections with different flexibility (e.g. floppy wire, soft wire, hard wire, super-hard wire etc.). The selection of wire is often dictated by the conditions on the way to a lesion to be treated and not by the lesion itself.

Once the leading wire is combined with the balloon, the freedom to select different types of wire is lost. One solution would be to multiply the line of crimped stent systems to have parallel systems with different wire tips. This is obviously a complex and costly solution. Thus, there is a need for a single operator stent system, which avoids this loss of freedom in an effective and cost efficient manner.

SUMMARY OF THE INVENTION

Embodiments of the stent system of the present invention preserve the choice of different wire flexibility in an economical fashion. In such embodiments a catheter may be made with only one lumen leading to the balloon. An arrangement is provided to easily lock a short wire in place at the distal end of the balloon. Multiple wires of different properties can be included in a package containing the stent and the delivery catheter, such that the physician will be able to choose the right wire tip according to the lesion and vessel treated and attach it at the distal tip of the balloon.

DETAILED DESCRIPTION

In today's catheterization lab, the interventional cardiologist has several choices to make in order best to optimize the equipment he is using to the conditions of the vessels he needs to treat. The relevant conditions that would determine the equipment used are the basic anatomy of the vessel both in the treated section and all the way from the entry point to the treated segment. Once a guiding catheter has been selected and inserted so that it engages the ostium of the treated coronary artery, the next choice is the guide wire to be used and then the balloon catheter and/or a pre-mounted stent system.

The choice of wire is critical for the probability of safely and optimally traversing the treated lesion with the wire and for lending the right support for the balloon catheter that needs to be threaded on the guide wire on its way to the lesion. Wires available for selection come in a variety of configurations and even any given single supplier of guide wires has three or more configurations that differ significantly in their properties. The properties of the different wires are selected by the cardiologist based on the tortuosity of the vessel, the length and tortuosity of the lesion and the rate of occlusion and nature (hardness) of the occlusive mass.

Thus, wires differ in their stiffness, in the length and combination of different sections of the wire and in the properties of the tip of the wire that is used to guide the wire into preferred branches in bifurcating vessels, but also to push against and penetrate total occlusions. The choice of wire is independent of the stent used and the freedom of separately optimizing the wire and the catheter or stent is important to cardiologists.

It is, thus, disadvantageous to make a delivery catheter integrated with a wire as in EP 1 101 455 A2, since it will deprive the physician of that freedom of choice.

Figure 1:
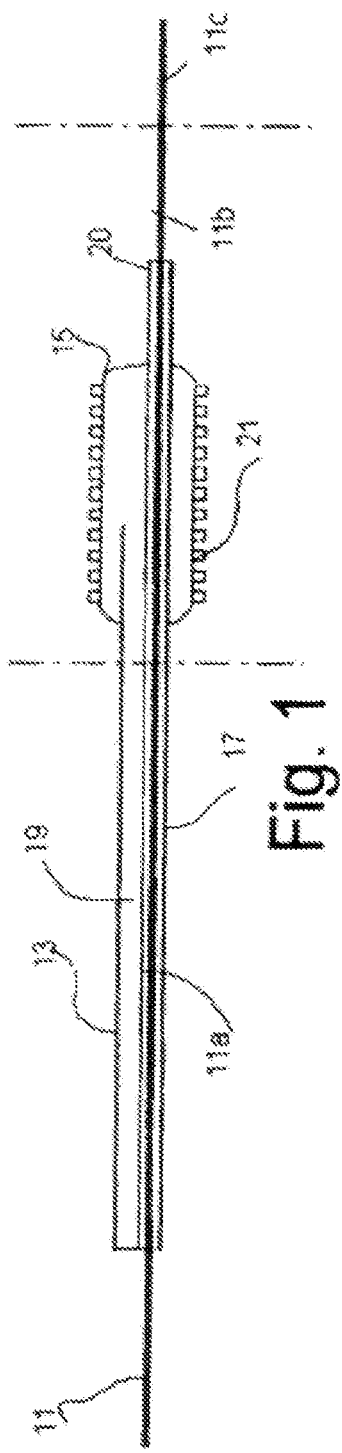
FIG. 1 is a schematic drawing of the prior art arrangement using a guide wire.

FIG. 1 illustrates, in schematic form, the typical present-day arrangement. A guide wire 11 is provided, which has been first inserted into the vessel to a position beyond the lesion to be treated. A catheter 13 with a stent on balloon section is threaded on the guide wire 11 by means of a first lumen 17 in the catheter. In some cases the separate guide wire is made of three sections of different flexibility, a stiff section 11a, a more flexible section 11b and most flexible and steerable section 11c. The stent on balloon section is at the distal end of the catheter 13 and includes a balloon 15 with a stent 21 crimped on it. A second lumen 19 is provided for inflating the balloon 15 in conventional fashion to expand the stent 21, once the stent and balloon have been guided to the lesion. There is a transition from catheter diameter to wire diameter at the tip 20 of the catheter 13 and it may undesirably latch on rough plaque or on struts of previously expanded stent when inserted through a stent. The catheter 13 with its own flexibility transition rides over the wire, with its variable flexibility, creating overall non-optimal flexibility.

Figure 2:
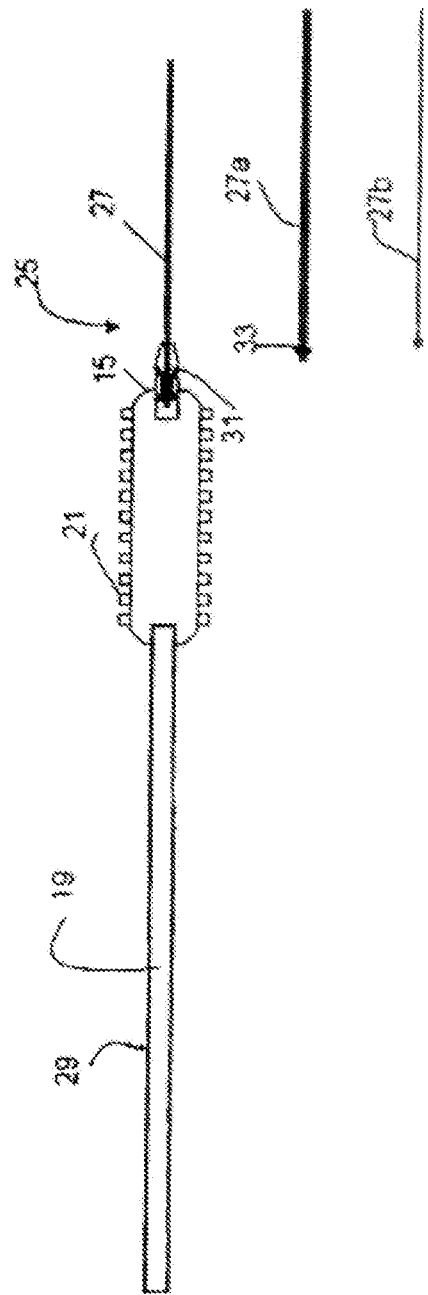
FIG. 2 is a schematic drawing of the single operator stent system of the present invention with interchangeable wire tips.

An embodiment of the present invention is schematically illustrated in FIG. 2. It has a delivery system whose forward tip 25 is made from a section of guide wire 27, which is like the tip of guide wire 11 of FIG. 1, combined with a catheter 29 with a lumen 19 only for inflating the balloon 15. A separate lumen for the guide wire is not needed. The flexibility transition is kept optimal, the profile of the system may be reduced and the problems of latching of the catheter tip are eliminated by a smooth transition in the tip 25. The wire 27 may typically be two to eight inches in length. Details of distal end of the catheter and stent on balloon section are not shown. These may be constructed in conventional fashion, for example, as shown in EP 1 101 445 A2, the disclosure of which is hereby incorporated by reference.

These may be constructed in conventional fashion, for example, as shown in EP 1 101 455 A2, the disclosure of which is hereby incorporated by reference.

In accordance with the embodiment of FIG. 2, a separate wire 27 is snapped or clipped on the catheter 29 at the distal end of the balloon 15. This wire may have areas of different flexibility just like the sections 11b and 11c of the embodiment shown in FIG. 1. Multiple wires 27, 27a, and 27b of different properties may be included with each catheter. These may be, e.g., floppy wire, soft wire, hard wire, super-hard wire etc. or wires having sections made up of two or more of these types of wire. Thus, embodiments of the present invention provide a stent system that preserves the ability to choose different wires in an economical fashion. An arrangement is provided to easily lock the short wire 27, 27a or 27b on the tip of the catheter 29. Specifically, in the illustrated embodiment, a receptacle into which said wires may be lockably inserted is provided.

Thus, in the illustrated arrangement, each of the wires of the set has a bead 33 on its end which snaps through a spring loaded member at the distal end of balloon 15 (it is to be understood that this is only one fast attachment mechanism and any other clip-on mechanism may be used in place of the one described above). Other manners of attachment will suggest themselves to those of skill in the art. A selection of multiple wires, (e.g. three wires 27, 27a or 27b) of different properties may be included in a package containing the stent and the delivery catheter. This insures that the physician will be able to choose the right wire tip, according to the lesion and vessel to be treated, and attach it to the distal tip of the balloon.

In use, once the proper wire tip has been selected, the physician inserts the catheter with the balloon, stent, and wire at its distal end into the vessel in the patient. He moves the stent to the lesion and then inflates the balloon to expand and deploy the stent at the lesion. The balloon is then deflated and the catheter, now with only the balloon and wire at its distal end, is removed.

The present invention recognizes that a wire tip of just a 2-8 inches is inexpensive. Thus, it may then be efficient to have the catheter and stent crimped on a balloon and to provide 3-4 different wire tips in the same package. The physician will select the right wire tip and click it into position at the distal end of the balloon prior to use.

Compared with an arrangement like that in EP 1 101 445 A2, this brings back the freedom to select the wire but by duplicating only an inexpensive component. It also gets away from a balloon combined with wire, as they are separate and for a good reason. It also makes the device much more useful and adaptable, but mainly much more acceptable to the potential user—the interventional cardiologist. The added price of a few wires is low enough to keep this solution within economic range and the mechanism of locking a wire into the balloon end is simple and can be done quickly enough as not to add significantly to the time or complexity of the procedure.

There is a trend for balloons on catheters become more and more of high Rated Burst Pressure (RBP) type and insertion of stents is becoming much like that of a balloon alone. As a result, the percentage of direct stenting, where no pre-dilatation is required, is increasing and it is expected to exceed 50% of all cases. In those cases there may not be a need for the insertion of more than one catheter. Thus, the advantage of having a wire in place on which to exchange catheters, as is the case now, should be diminished. Embodiments of the present invention are particularly well suited in such cases.

The wire 27, 27a or 27b at the forward section of the single operator stent system of the present invention may include a balloon or another device for distal protection. It may be expanded or deployed for protection against particles released during the deployment of the stent being swept downstream in a manner known in the art. These and other modifications can be made without departing from the spirit of the invention, which is intended to be limited solely by the appended claims.

What is claimed is:

1. A stent system comprising:
   a catheter with a lumen;
   a balloon in communication with said lumen disposed at the distal end of said catheter;
   a stent disposed over said balloon; and
   an arrangement located at the distal end of said balloon, said arrangement to receive and removably lock a wire to said arrangement.

2. The stent according to claim 1 wherein said catheter has only one lumen.

3. The stent system according to claim 2 and further including multiple wires of different properties.

4. The stent system according to claim 3 wherein said multiple wires of different properties includes a wire having areas of different flexibility.

5. The stent system according to claim 4 wherein said wire having areas of different flexibility has a stiff section, a more flexible section and most flexible section.

6. The stent system according to claim 5 wherein one of said areas is more steerable.

7. The stent system according to claim 4 wherein said multiple wires of different properties include wires selected from the group consisting of floppy wire, soft wire, hard wire, super-hard wire and wires having sections made up of two or more of these types of wire.

8. The stent system according to claim 4 and wherein said arrangement comprises a receptacle into which said wires may be lockably inserted.

9. The stent system according to claim 1 wherein said arrangement comprises a spring loaded member at the distal end of said balloon, and each of the wires has a bead on its end which snaps through and is retained by said spring loaded member.

10. The stent system according to claim 9 wherein at least three different wires are provided.

11. The stent system according to claim 4 wherein said multiple wires comprise a wire tip of about 2-8 inches.

12. The stent system according to claim 1 wherein said balloon has a Rated Burst Pressure (RBP) sufficient for direct stenting.

13. A stent system comprising:
a catheter with a lumen;
a balloon having an inside in communication with said lumen disposed at the distal end of said catheter, such that the balloon can be inflated by fluid pressure supplied through said lumen;
a stent disposed over said balloon; and
a locking mechanism at the distal end of the balloon, and a wire removably locked to the distal end of the balloon.

14. The stent system according to claim 13 wherein said catheter has only one lumen.

15. The stent system according to claim 13 wherein said balloon has a high Rated Burst Pressure (RBP).

* * * * *